United States Patent [19]

Hittmair et al.

[11] 4,035,453

[45] July 12, 1977

[54] DENTAL IMPRESSION MATERIALS

[75] Inventors: Paul Hittmair; Wolfgang Hechtl; Eckhart Louis; Ernst Wohlfarth, all of Burghausen, Germany

[73] Assignee: Wacker-Chemie GmbH, Munich, Germany

[21] Appl. No.: 629,344

[22] Filed: Nov. 6, 1975

Related U.S. Application Data

[62] Division of Ser. No. 473,452, May 28, 1974, Pat. No. 3,950,300, which is a division of Ser. No. 405,338, Oct. 11, 1973, abandoned.

[51] Int. Cl.² .................................... A61C 13/00
[52] U.S. Cl. .................................... 264/16; 32/15; 260/29.1 SB; 260/37 SB; 260/46.5 UA; 260/46.5 G; 260/46.5 H; 260/827; 264/17; 264/18
[58] Field of Search .......... 32/15; 260/37 SB, 82.7, 260/29.1 SB, 46.5 UA, 46.5 H, 46.5 G; 264/16, 17, 18

[56] References Cited
U.S. PATENT DOCUMENTS

| | | | |
|---|---|---|---|
| 3,271,362 | 9/1966 | Chalk et al. | 260/46.5 UA |
| 3,474,123 | 10/1969 | Kelly et al. | 260/46.5 UA |
| 3,516,946 | 6/1970 | Modic | 260/46.5 UA |
| 3,527,655 | 9/1970 | Ballard | 260/46.5 UA |
| 3,647,725 | 3/1972 | Nitzsche et al. | 260/46.5 G |
| 3,697,473 | 10/1972 | Polmanteer et al. | 260/46.5 UA |
| 3,715,334 | 2/1973 | Karstedt | 260/46.5 UA |
| 3,732,330 | 5/1973 | Mink et al. | 260/825 |
| 3,775,452 | 11/1973 | Karstedt | 260/46.5 UA |
| 3,814,730 | 6/1974 | Karstedt | 260/46.5 UA |
| 3,950,300 | 4/1976 | Hittmair et al. | 260/827 |

*Primary Examiner*—Melvyn I. Marquis

[57] ABSTRACT

The invention relates to a method for preparing a dental impression which comprises applying a dental impression material to a tooth of which an impression is to be taken, curing the material and thereafter removing the resulting impression from the tooth, said dental impression material being a mixture of a. a diorganopolysiloxane containing terminal triorganosiloxy groups in which at least one vinyl group is present in each of the triorganosiloxy groups,
b. an organopolysiloxane having at least three Si-bonded hydrogen atoms per molecule,
c. a catalyst capable of promoting the addition of Si-bonded hydrogen to vinyl groups at room temperature and, if desired,
d. additives such as fillers, pigments, flavoring substances and plasticizers.

32 Claims, No Drawings

DENTAL IMPRESSION MATERIALS

This is a division, of application Ser. No. 473,452, filed May 28, 1974 now U.S. Pat. No. 3,950,300 which in turn is a division of Ser. No. 405,338 filed Oct. 11, 1973 now abandoned.

The present invention relates to dental impression materials, and more particularly to a combination of substances (hereinafter called 'base materials') suitable for the preparation at room temperature of dental impression materials.

Dental impression materials are materials that are used in dentistry or odontology for taking impressions of human or animal teeth. These materials are brought into contact with the teeth of which an impression is to be taken for a period of not more than 10 minutes, during which time they should harden; the hardened product should be easily removable from the teeth.

Dental impression materials can be prepared from mixtures of (i) diorganopolysiloxanes having end groups capable of condensation, (ii) organopolysiloxanes having at least three Si-bonded hydrogen atoms per molecule, and (iii) condensation catalysts (cf. German Auslegeschrift No. 1,163,021). On hardening, such a mixture gives off hydrogen, which can lead to surface irregularities of, for example, plaster of paris casts taken from the impressions.

Another mixture which is extensively used for the preparation of dental impression materials is a mixture of (i) diorganopolysiloxanes having condensable end groups, (ii) silicon compounds having, per molecule, at least three hydrogen groups bonded through oxygen to silicon, and (iii) condensation catalysts (cf. German Specification cited above). This mixture has the disadvantages that it contains substances corrosive to, for example, aluminium foil, and that the silicon compounds (ii) are moisture-sensitive. These properties make packaging of the material difficult, since the packages used are often of plastics materials, such as polyethylene, that are not completely impervious to moisture, often with the conjoint use of aluminium foil.

It has now been found that mixtures of (i) organopolysiloxanes containing alkenyl groups and (ii) organopolysiloxanes containing Si-bonded hydrogen, together with (iii) condensation catalysts, have various advantages over the mixtures mentioned above. Thus, hydrogen is not given off on hardening this mixture, and the mixture does not contain moisture-sensitive components, and contains fewer or no corrosive components. These mixtures, which will harden at room temperature to give elastomers, also have the advantage of having a linear shrinkage on hardening of less than 0.1%, thus giving a particularly high accuracy of impression.

The present invention therefore provides, according to one embodiment, a pack of substances suitable for the preparation of a dental impression material, which pack comprises a. a diorganopolysiloxane having, as terminal units, triorganosiloxy groups each having at least one vinyl group,
b. an organopolysiloxane having at least three Si-bonded hydrogen atoms per molecule,
c. a catalyst capable of promoting the addition of Si-bonded hydrogen to vinyl groups at room temperature, and optionally
d. customary additives, in which pack components (b) and (c) are kept separate from each other, the pack advantageously being provided with instructions to admix the various components and to use the resulting mixture as a dental impression material, by bringing it into contact with the tooth or teeth of which an impression is to be taken, and leaving it to harden.

According to another embodiment of the invention, there is provided a method of making a dental impression material, which comprises preparing a mixture of components (a), (b), (c), and optionally (d), specified above.

According to a further embodiment of the invention, there is provided a dental impression material, which comprises components (a), (b), (c), and optionally (d), in admixture with each other.

According to a further embodiment, the invention provides a method of making a dental impression which comprises bringing a mixture of components (a), (b), (c), and optionally (d), into contact with the tooth or teeth of which an impression is to be taken, leaving the mixture to harden, and removing the resulting impression from the tooth or teeth.

The invention also provides, according to a yet further embodiment, a dental impression prepared from a mixture of components (a), (b), (c), and optionally (d).

Component (a), used according to the invention, is a diorganopolysiloxane having terminal units that are triorganosiloxy groups in which at least one of the three organic radicals is a vinyl group. Preferred diorganopolysiloxanes of this type are those of the general formula

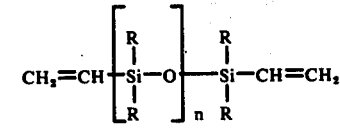

in which each R denotes an unsubstituted or substituted monovalent hydrocarbon radical free of aliphatic multiple bonds, and $n$ denotes an integer. At least 50% of the radicals R are preferably methyl radicals, and examples of other suitable radicals R are ethyl, phenyl and 3,3,3-trifluoropropyl radicals. The value of $n$ should be such that the polymer has a viscosity at 25° C of from 500 to 300,000 cP, preferably not more than 100,000 cP.

Component (b) is an organopolysiloxane having at least three Si-bonded hydrogen atoms per molecule. Suitably, this organopolysiloxane contains from 0.01 to 1.7% by weight of Si-bonded hydrogen atoms, and the silicon valencies not satisfied by hydrogen atoms, or siloxane oxygen atoms are satisfied by unsubstituted or substituted monovalent hydrocarbon radicals free of aliphatic multiple bonds, at least 50 percent of the hydrocarbon radicals bonded to silicon atoms carrying hydrogen atoms being methyl radicals.

Component (c) is a catalyst that will promote the addition of Si-bonded hydrogen to vinyl groups at room temperature. The most suitable catalysts are platinum and its compounds, especially platinum-siloxane complexes. Suitable platinum-siloxane complexes are those that contain inorganic halogen in such amount that the average ratio of gram atom of halogen to gram atom of platinum is not more than 1:1, and that consist essentially of chemically combined platinum and an organopolysiloxane of units of the formula $$R_a R'_b R''_c SiO_{(4-a-b-c)/2}$$

in which R has the meaning given above, R' denotes a monovalent optionally halogenated hydrocarbon radical having one or more aliphatic multiple bonds (for example, an ethynyl, prop-1-ynyl, or vinyl radical), R" denotes an R' radical chemically bonded to platinum, each of $a$ and $b$ has a value from 0 to 2 inclusive, $c$ has a value from 0.0002 to 3 inclusive, and the sum of $a$, $b$ and $c$ is from 1 to 3 inclusive. Such platinum-siloxane complexes, like all the other materials mentioned, have been previously described (see, for example, German Offenlegungsschrift No. 1,668,159 and U.K. Pat. Specification No. 1,211,699). Important examples of these platinum complexes are those in which platinum is chemically bonded to 1,3-divinyl tetramethyldisiloxane.

Platinum and platinum compounds are appropriately used in amounts of from 5 to 500 ppm (parts by weight per million), preferably from 5 to 100 ppm, calculated as Pt and relative to the total weight of the various components used.

Instead of the platinum complexes described above, or in combination with such complexes, it is of course also possible to use other hardening catalysts that promote the addition of Si-bonded hydrogen to vinyl groups at room temperature within whatever time is acceptable for the particular field of use in making dental impressions, provided these other catalysts are not toxic or that their toxicity is not objectionable in the particular field of use in making dental impressions. Examples of such other hardening catalysts are cobalt carbonyls and manganese carbonyls.

Component (d), if present, consists of customary additives. These are, in particular, fillers, and also pigments, soluble dyestuffs, flavouring substances, scents, and plasticisers, for example. The fillers can be reinforcing and/or non-reinforcing fillers.

Examples of reinforcing fillers, that is fillers with a surface area of at least 50 m²/g, are pyrogenically produced silicon dioxide, silicon dioxide aerogels, that is to say silicic acid hydrogels dehydrated so as to maintain the structure, and precipitated silicon dioxide. Examples of non-reinforcing fillers, that is fillers having a surface area of less than 50 m²/g, are calcium carbonate, quartz powder, diatomaceous earth, titanium dioxide, zirconium silicate, aluminium silicate, zinc oxide, plaster of paris, so-called "molecular sieves", and asbestine, that is to say a magnesium-calcium silicate which resembles talc. All these fillers, but especially the reinforcng fillers, can have organosilyl groups on their surface if they have been pretreated, for example, with trimethylhalogenosilanes, as described in, for example, U.S. Pat. Specification No. 2,610,167, or if they have been manufactured, for example, by reaction of aqueous silica sols with organohalogenosilanes, or have been rendered hydrophobic in some other way. Mixtures of different fillers can be used.

Preferably, the fillers are used in amounts of from 1 to 90% by weight, especially from 5 to 90% by weight, relative to the total weight of components. Non-reinforcing fillers are appropriately used in amounts of at least 20% by weight, relative to the total weight of all organopolysiloxanes present, whereas reinforcing fillers are appropriately used in amounts of from 1 to 10% by weight, relative to the total weight of all organopolysiloxanes present. It is, however, possible to use larger amounts of reinforcing fillers provided that the miscibility of the compositions does not suffer as a result; amounts of reinforcing fillers larger than 10 percent by weight are, for example, possible if the fillers have been manufactured by the reaction of aqueous silica sols with organohalogenosilanes.

Plasticisers that may be present in component (d) include, for example, organopolysiloxanes free of aliphatic multiple bonds and Si-bonded hydrogen, for example dimethylpolysiloxanes that are liquid at room temperature and are end-blocked by trimethylsiloxy groups. Copolymers of units of the formulae $$SiO_{4/2} \quad (I)$$
$$(CH_3)_3SiO_{1/2} \quad (II)$$

and $$(CH_3)_2(CH_2=CH)SiO_{1/2} \quad (III)$$

containing from 1.5 to 3.5% by weight of vinyl groups and a total of from 0.6 to 1 of units (II) and (III) per unit (I) are also suitable as plasticisers, as are organopolysiloxanes having two Si-bonded hydrogen atoms per molecule, with no more than one hydrogen atom being bonded to any one silicon atom, having no more than 500 silicon atoms per molecule, and having methyl, ethyl, phenyl and/or 3,3,3-trifluoropropyl radicals as the organic radicals. Purely organic resins, for example PVC powder, are also suitable as plasticisers.

The relative amounts of components (a), (b), and (d) used in preparing the dental impression materials according to the invention are appropriately such that a total of from 0.75 to 5 gram atoms of Si-bonded hydrogen is present from component (b) and optionally component (d) per gram molecule of vinyl group present from component (a) and optionally component (d).

As mentioned previously, according to one embodiment of the present invention, the various components used for making the dental impression material may be made up into a pack. In such a pack components (b) and (c) must be kept separate from one another, else Si-bonded hydrogen will be eliminated from component (b). Apart from this limitation the various components may be admixed or kept separate as desired. The pack will normally have just two separate compartments, although more compartments may be used if desired. The components may be divided among the two compartments in various ways: thus, for example, one compartment may contain components (a) and (c), while a second compartment contains all remaining components including component (b); alternatively, one compartment may contain components (a) and (b), together with any organopolysiloxanes present as component (d), while a second compartment contains all remaining components including component (c) and, for example, any filler that may be present as component (d).

In order to obtain impressions with as low a shrinkage as possible, the catalyst, component (c), should advantageously be used free, or almost free, of solvent. However, in order to aid a uniform distribution of the catalyst in the mixture of other components, when all the components are mixed immediately prior to use, the catalyst is advantageously packed in admixture with a diluent. This diluent may suitably be the diorganopolysiloxanes, component (a), or other organopolysiloxanes containing vinyl groups, present as component (d), or fillers, present as component (d), or mixtures thereof.

In the packs according to 29 invention the various components are advantageously present in the relative amounts and absolute amounts in which it is eventually desired to use them, thus saving the dentist or odontologist the bother of measuring out the components, together with the attendant possibility of errors.

Various types of packages are suitable for containing the components in the packs according to the invention; they generally consist of a container separated into compartments by a foil that can be easily destroyed. Such packages are described in, for example, U.S. Pat. Specification No. 3,067,606.

One example of such a package is a tube having a sealed opening at one end, and containing two compartments separated by an aluminium foil, with a twirler-like piston projecting through the seal of the opening of the tube, by means of which piston the foil can be perforated and the contents of the two compartments can be mixed with one another. The tube may be of, for example, a plastic material, such as polyethylene, optionally covered with aluminium foil. Another example of a suitable package is a container equipped with a hollow stirrer which contains, for example, catalyst, between two partitioning devices for example films or plugs, that can be perforated or expelled by means of a rod, whilst the container contains the remaining components. Also suitable is a plastics container, optionally equipped with a stirrer, into which, in use, the catalyst is introduced through the wall, by means of an injection syringe. Such packages are described in, for example, Canadian Pat. specification 746,989.

In order to prepare the dental impression material according to the invention, the components (a), (b), (c) and optionally (d) are normally mixed at environmental temperatures and pressures, that is to say in most cases at from 10° to 25° C and about 760 mm Hg (absolute). The dental impression materials according to the invention can be used in accordance with the conventional methods of working when using dental impression materials, and employing the devices customary for the purpose.

The following Example was carried out to illustrate the present invention. The parts are parts by weight.

A mixture of a platinum-siloxane complex and a diluent was prepared as follows: 20 parts of sodium bicarbonate were added to a mixture of 10 parts of $H_2PtCl_6.8H_2O$, 20 parts of 1,3-divinyltetramethyldisiloxane, and 50 parts of ethanol. The mixture was heated to boiling under reflux for 30 minutes whilst stirring and was then left to stand for 15 hours and filtered. The volatile constituents were distilled from the filtrate at about 12 mm Hg (absolute). 17 parts of a liquid were obtained as the residue and were dissolved in benzene. The solution was filtered and the benzene was distilled from the filtrate. The residue was mixed with dimethylpolysiloxane containing vinyldimethylsiloxy groups as terminal units and having a viscosity of 1400 cP at 23° C, as the diluent, in such an amount that the mixture contained 1 percent by weight of Pt.

A pack of component for the preparation of a dental impression material was prepared as follows: 600 parts of dimethylpolysiloxane containing vinyldimethylsiloxy groups as terminal units and having a viscosity of 1400 cP at 23° C were mixed with 200 parts of quartz powder and 100 parts of calcium carbonate powder. 100 parts of this mixture were mixed with 0.3 part of the mixture of platinum-siloxane complex and diluent described above. 10 parts of the mixture thus obtained were introduced into one compartment of a package containing two compartments separated by an aluminum foil. 1 Part of a copolymer of dimethylsiloxane, methylhydrogenosiloxane and trimethylsiloxane units, with a ratio of the dimethylsiloxane units to the methylhydrogenosiloxane units of 12:1 and a viscosity of 3000 cP at 23° C was introduced into the other compartment of the package.

After a storage period of one year, the contents of the two compartments of the package were mixed. The composition thus obtained had a so-called "pot-life" (that is to say the time available for shaping the material, between its preparation and the perceptible start of hardening) of 3 minutes. It was used to produce a so-called "ring impression" of a ground-down tooth into which a gold pin had been set, in the mouth of a test person. The resulting fully hardened, non-tacky and elastic impression was taken out of the mouth after a total of about 6 minutes after preparation of the composition.

The pot life and the hardening time were found to be identical for a freshly prepared composition, thus showing that no change in the hardening characteristics of the composition occurred on storage. After storing both impressions for eight days, the linear shrinkage was measured. It was only 0.06%.

What we claim is:

1. A method of making a dental impression which comprises (1) applying to a tooth of which an impression is to be taken, an impression material which is obtained by mixing (a) a diorganopolysiloxane containing triorganosiloxy terminal units, each of which contains at least one vinyl group, and having a viscosity of from 500 to 300,000 cP at 25° C. with (b) an organopolysiloxane free of aliphatic multiple bonds and having at least three Si-bonded hydrogen atoms per molecule and having from 0.01 to 1.7 percent by weight of Si-bonded hydrogen atoms in which the silicon valences not satisfied by hydrogen atoms or siloxane oxygen atoms are satisfied by unsubstituted and substituted monovalent hydrocarbon radicals free of aliphatic multiple bonds and in which at least 50 percent of the hydrocarbon radicals bonded to silicon atoms carrying hydrogen atoms are methyl radicals, said organopolysiloxane (b) being present in an amount so that a total of 0.75 to 5 gram atoms of Si-bonded hydrogen is present per gram molecule of vinyl group and (c) a catalyst which is capable of promoting the addition of Si-bonded hydrogen to vinyl groups at room temperature, said catalyst is selected from the group consisting of platinum, platinum compounds, platinum complexes, cobalt carbonyls and manganese carbonyls (2) allowing the material to harden and thereafter (3) removing the resultant impression from the tooth.

2. The method of claim 1 wherein the impression material contains an additive (d) which is selected from the group consisting of a filler and a plasticiser selected from the class consisting of trimethylsiloxy endblocked organopolysiloxanes free of aliphatic multiple bonds and Si-bonded hydrogen atoms, copolymers of units of the formula (1) $SiO_{4/2}$, (II) $(CH_3)_3SiO_{1/2}$ and (III) $(CH_3)_2(CH_2\!\!=\!\!CH)SiO_{1/2}$ containing from 1.5 to 3.5 percent by weight of vinyl groups and a total of from 0.6 to 1 of units (II) and (III) per unit of (I), organopolysiloxanes containing two Si-bonded hydrogen atoms per molecule with no more than one hydrogen atom being connected to any 1 silicon atom and having up to 500 silicon atoms per molecule in which the orgainc radicals are selected from the group consisting of methyl, ethyl, phenyl and 3,3,3-trifluoropropyl radicals and organic resins.

3. The dental impression prepared by the method of claim 1.

4. The method of claim 2 wherein the organic resin is polyvinyl chloride.

5. The method of claim 1 wherein the dental impression material also contains an additive (d) which is selected from the group consisting of a filler, a pigment, a soluble dyestuff, a flavoring substance, a scent, a plasticiser and mixtures thereof.

6. The method of claim 5 wherein the plasticiser is an organopolysiloxane free of aliphatic multiple bonds and of Si-bonded hydrogen atoms.

7. The method of claim 5 wherein the filler is a reinforcing filler having a surface area of at least 50 m²/g.

8. The method of claim 7 wherein the amount of reinforcing filler is from 1 to 10 percent by weight based on the total weight of the organopolysiloxanes.

9. The method of claim 7 wherein the filler has been treated to provide organosilyl groups on its surface.

10. The method of claim 7 wherein the amount of filler is from 1 to 90 percent by weight based on the total weight of the components.

11. The method of claim 1 wherein component (a) is a diorganopolysiloxane having a viscosity at 25° C. of from 500 to 300,000 cP and being of the general formula

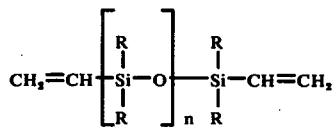

in which each R is selected from the group consisting of unsubstituted and substituted monovalent hydrocarbon radicals free of aliphatic multiple bonds and $n$ denotes an integer.

12. The method of claim 1 wherein component (b) is an organopolysiloxane having at least three Si-bonded hydrogen atoms per molecule and having from 0.01 to 1.7 percent by weight of Si-bonded hydrogen atoms, in which the silicon valences not satisfied by hydrogen atoms or siloxane oxygen atoms are satisfied by unsubstituted or substituted monovalent hydrocarbon radicals free of aliphatic multiple bonds, and in which at least 50 percent of the hydrocarbon radicals bonded to silicon atoms carrying hydrogen atoms are methyl radicals.

13. The method of claim 1 wherein component (c) is selected from the class consisting of platinum, platinum compounds, a cobalt carbonyl compound and a manganese carbonyl compound.

14. The method of claim 13 wherein the amount of component (c) is from 5 to 500 ppm platinum based on the total weight of the components.

15. The method of claim 1 wherein the relative amounts of components (a), (b) and (d) are such that a total of from 0.75 to 5 gram atoms of Si-bonded hydrogen is present per gram molecule of vinyl group.

16. The method of claim 5 wherein the plasticiser is a dimethylpolysiloxane liquid at room temperature which is endblocked by trimethylsiloxy groups.

17. The method of claim 5 wherein the plasticiser is a copolymer comprising units of the formula

and

and containing from 1.5 to 3.5 percent by weight of vinyl groups and a total of from 0.6 to 1 of units (II) and (III) per unit (I).

18. The method of claim 5 wherein the plasticiser is an organopolysiloxane having up to 500 silicon atoms per molecule and having two Si-bonded hydrogen atoms per molecule with no more than one hydrogen atom being bonded to any one silicon atom and the remaining organic radicals being selected from the class consisting of methyl, ethyl, phenyl and/or 3,3,3-trifluoropropyl radicals.

19. The method of claim 5 wherein the plasticiser is an organic resin.

20. The method of claim 5 wherein the plasticiser is polyvinyl chloride.

21. The method of claim 7 wherein the filler is selected from the group consisting of pyrogenically-produced silicon dioxide, silicon dioxide aerogels and precipitated silicon dioxide.

22. The method of claim 5 wherein the filler is a nonreinforcing filler having a surface area less than 50 m²/g.

23. The method of claim 22 wherein the filler is selected from the class consisting of calcium carbonate, quartz powder, diatomaceous earth, titanium dioxide, zirconium silicate, aluminum silicate, zinc oxide, plaster of paris, a molecular sieve and asbestine.

24. The method of claim 22 wherein the amount of nonreinforcing filler is at least 20 percent by weight based on the total weight of the organopolysiloxanes.

25. The method of claim 22 wherein the filler has been treated to provide organosilyl groups on its surface.

26. The method of claim 10 wherein the amount of filler is from 5 to 90 percent by weight based on the total weight of the components.

27. The method of claim 11 wherein the unsubstituted monovalent hydrocarbon radicals are selected from the group consisting of methyl, ethyl, phenyl and the substituted monovalent hydrocarbon radical is 3,3,3-trifluoropropyl.

28. The method of claim 11 wherein the diorganopolysiloxane has a viscosity at 25° C. of from 500 to 100,000 cP.

29. The method of claim 28 wherein the platinum compound is a platinum-siloxane complex.

30. The method of claim 29 wherein the platinum-siloxane complex contains an inorganic halogen in which the halogen is present in such an amount that the average ratio of gram atom of halogen to gram atom of platinum is not more than 1:1, and consists essentially of units of the formula

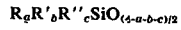

in which R is selected from the class consisting of unsubstituted and substituted monovalent hydrocarbon radicals free of aliphatic multiple bonds, R' is selected from the class consisting of monovalent hydrocarbon radicals and halogenated monovalent hydrocarbon radicals having one or more aliphatic multiple bonds, R'' represents and R' radical chemically bonded to platinum, each of $a$ and $b$ has a value of from 0 to 2, $c$ has a value of from 0.0002 to 3, and the sum of $a$, $b$ and $c$ is from 1 to 3.

31. The method of claim 29, wherein the platinum-siloxane complex is platinum-1,3-divinyltetramethyl-disiloxane.

32. The method of claim 29 wherein the amount of component (c) is from 5 to 100 ppm platinum based on the total weight of the components.

* * * * *